(12) United States Patent
Shinohara et al.

(10) Patent No.: US 10,873,081 B2
(45) Date of Patent: *Dec. 22, 2020

(54) ELECTRODE MATERIAL

(71) Applicants: TATSUTA ELECTRIC WIRE & CABLE CO., LTD., Osaka (JP); FUJI SILYSIA CHEMICAL LTD., Aichi (JP)

(72) Inventors: Keisho Shinohara, Kyoto (JP); Takashi Morita, Kyoto (JP); Shinji Yoshino, Kyoto (JP); Mitsuteru Ogawa, Aichi (JP); Mitsuhiro Kamimura, Aichi (JP)

(73) Assignees: TATSUTA ELECTRIC WIRE & CABLE CO., LTD., Osaka (JP); FUJI SILYSIA CHEMICAL LTD., Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/311,444

(22) PCT Filed: Jun. 23, 2017

(86) PCT No.: PCT/JP2017/023228
§ 371 (c)(1),
(2) Date: Dec. 19, 2018

(87) PCT Pub. No.: WO2018/003698
PCT Pub. Date: Jan. 4, 2018

(65) Prior Publication Data
US 2019/0312275 A1     Oct. 10, 2019

(30) Foreign Application Priority Data

Jun. 30, 2016   (JP) .................. 2016-130496

(51) Int. Cl.
*C01B 33/12* (2006.01)
*C01G 5/02* (2006.01)
(Continued)

(52) U.S. Cl.
CPC .......... *H01M 4/582* (2013.01); *A61B 5/0408* (2013.01); *C01B 33/12* (2013.01); *C01G 5/02* (2013.01)

(58) Field of Classification Search
None
See application file for complete search history.

(56) References Cited

U.S. PATENT DOCUMENTS 4,270,543 A   6/1981  Tabuchi
5,565,143 A  10/1996  Chan
(Continued)

FOREIGN PATENT DOCUMENTS

EP   2000173 A2   12/2008
JP  51026789 A    3/1976
(Continued)

OTHER PUBLICATIONS

Mert Tuncer. "Effects of Chloride Ion and the Types of Oxides on the Antibacterial Activities of Inorganic Oxide Supported AG Materials". July 2007. Izmir Institute of Technology. (Year: 2007).*

(Continued)

*Primary Examiner* — Haroon S. Sheikh
(74) *Attorney, Agent, or Firm* — Rankin, Hill & Clark LLP

(57) ABSTRACT

An electrode material (1) includes: a porous support (2); and silver chloride (4) supported on the porous support (2). The porous support (2) is, for example, silica. The silica may be: wet-process silica such as precipitated silica or gelation method silica; dry-process silica; or the like.

3 Claims, 2 Drawing Sheets

(51) Int. Cl.
  *H01M 4/58* (2010.01)
  *A61B 5/0408* (2006.01)

(56) References Cited

U.S. PATENT DOCUMENTS

| | | | |
|---|---|---|---|
| 5,851,438 | A | 12/1998 | Chan |
| 10,629,325 | B2* | 4/2020 | Shinohara ............ A61B 5/0408 |
| 2001/0031988 | A1 | 10/2001 | Kurata |
| 2003/0051799 | A1 | 3/2003 | Stevenson |
| 2014/0081118 | A1 | 3/2014 | Reinhold, Jr. |
| 2018/0215941 | A1 | 8/2018 | Hagar |

FOREIGN PATENT DOCUMENTS

| | | | |
|---|---|---|---|
| JP | 53-19870 | A | 2/1978 |
| JP | 57021302 | U1 | 2/1982 |
| JP | 58007227 | A | 1/1983 |
| JP | 59190649 | A | 10/1984 |
| JP | S6410164 | A | 1/1989 |
| JP | H05095922 | A | 4/1993 |
| JP | 05176904 | A | 7/1993 |
| JP | 05182513 | A | 7/1993 |
| JP | 2001292972 | A | 10/2001 |
| JP | 2007085763 | A | 4/2007 |
| JP | 2012-91358 | A | 5/2012 |
| JP | 2014517759 | A | 7/2014 |
| JP | 2015210883 | A | 11/2015 |
| JP | 2018168445 | A | 11/2018 |
| WO | 2001004614 | A1 | 1/2001 |
| WO | 2007111368 | A1 | 10/2007 |
| WO | 2014/129597 | A1 | 8/2014 |
| WO | 2015162931 | A1 | 10/2015 |

OTHER PUBLICATIONS

Min. "Development of white antibacterial pigment based on silver chloride nanoparticles and mesopourous silica and its polymer composite" (Year: 2015).*
International Search Report dated Sep. 12, 2017 filed in PCT/JP2017/023234.
International Preliminary Report on Patentability dated Jan. 10, 2019 filed in PCT/JP2017/023234.
T. Endo et al. "Preparation and Catalytic Activities of Noble Metal Binary Particle Dendrimer Nanocomposites", Journal of the Japan Society of Colour Material, 2005, pp. 185-190, vol. 78, No. 4, Japan Society of Colour Material, Japan; Partial translation.
International Search Report dated Aug. 8, 2017 filed in PCT/JP2017/023228.
International Preliminary Report on Patentability dated Jan. 10, 2019 filed in PCT/JP2017/023228.
International Preliminary Report on Patentability dated Jan. 10, 2019 filed in PCT/JP2017/023226.
International Search Report dated Sep. 26, 2017 filed in PCT/JP2017/023226.
Office Action dated Oct. 15, 2019 for co-pending U.S. Appl. No. 16/309,729.
Office Action dated Apr. 15, 2019 filed in co-pending U.S. Appl. No. 16/309,729.
Japanese Office Action (JPOA) dated Jun. 9, 2020 issued in Japanese Patent Application No. 2018-525134 which corresponds to U.S. Appl. No. 16/311,334; English translation thereof.

* cited by examiner

ELECTRODE MATERIAL

TECHNICAL FIELD

The present invention relates to an electrode material.

BACKGROUND ART

Patent Literature 1 discloses a bioelectrode that includes a nonpolarizable electrode containing silver and silver chloride. As such, silver, silver chloride, and the like are known to be used as electrode materials.

CITATION LIST

Patent Literature

[Patent Literature 1]
Japanese Patent Application Publication, Tokukaihei, No. 5-95922

SUMMARY OF INVENTION

Technical Problem

Silver chloride is photosensitive. Therefore, silver chloride readily decomposes upon irradiation with light, and its color turns purple and then black during the reduction into silver. As such, electrode materials composed of silver chloride have an issue in that their properties are prone to change.

An object of the present invention is to provide an electrode material with improved light resistance as compared to electrode materials composed of silver chloride.

Solution to Problem

In order to attain the above object, a subject matter in accordance with Aspect 1 of the present invention is an electrode material that includes: a porous support; and silver chloride supported on the porous support.

According to the above arrangement, silver chloride supported on the walls of pores (cavities) in the porous support does not receive much light. Therefore, the electrode material of this arrangement has improved light resistance as compared to the conventional electrode material composed of silver chloride powder.

DESCRIPTION OF EMBODIMENTS

An electrode material according to one or more embodiments of the present invention contains: a porous support; and silver chloride (AgCl) supported on the porous support.

An electrode material in accordance with the present embodiment is advantageous in the following aspects.

According to the electrode material in accordance with the present embodiment, silver chloride supported on the walls of pores (cavities) in the porous support does not receive much light. Therefore, the electrode material in accordance with the present embodiment has improved light resistance as compared to the conventional electrode material composed of fine silver chloride particles.

The electrode material in accordance with the present embodiment is such that silver chloride is supported on a surface of a porous support (including the walls of pores). This makes it possible to increase the surface area of silver chloride as compared to the conventional electrode material composed of silver chloride, when the electrode material in accordance with the present embodiment and the conventional electrode material composed of silver chloride are equal in the total amount of silver chloride in the electrode material.

The electrode material in accordance with the present embodiment is such that silver chloride is supported on a surface of a porous support. This makes it possible to reduce the amount of silver chloride (or silver) as compared to the electrode material composed of silver chloride, when the electrode material in accordance with the present embodiment and the electrode material composed of silver chloride are to achieve the same total area of exposure of silver chloride within the electrode material. This makes it possible to provide a less expensive electrode material.

The porous support is, for example, silica (silicon dioxide). Silver chloride agglomerates easily (has low dispersibility), whereas silica does not easily agglomerate (has high dispersibility). Therefore, when silica is used as the porous support, the resulting electrode material has high dispersibility. The silica may be wet-process silica such as precipitated silica or gelation method silica (gel method silica), or may be dry-process silica. The silica is preferably gelation method silica. In this embodiment, the silica is gelation method silica.

Figure 1:
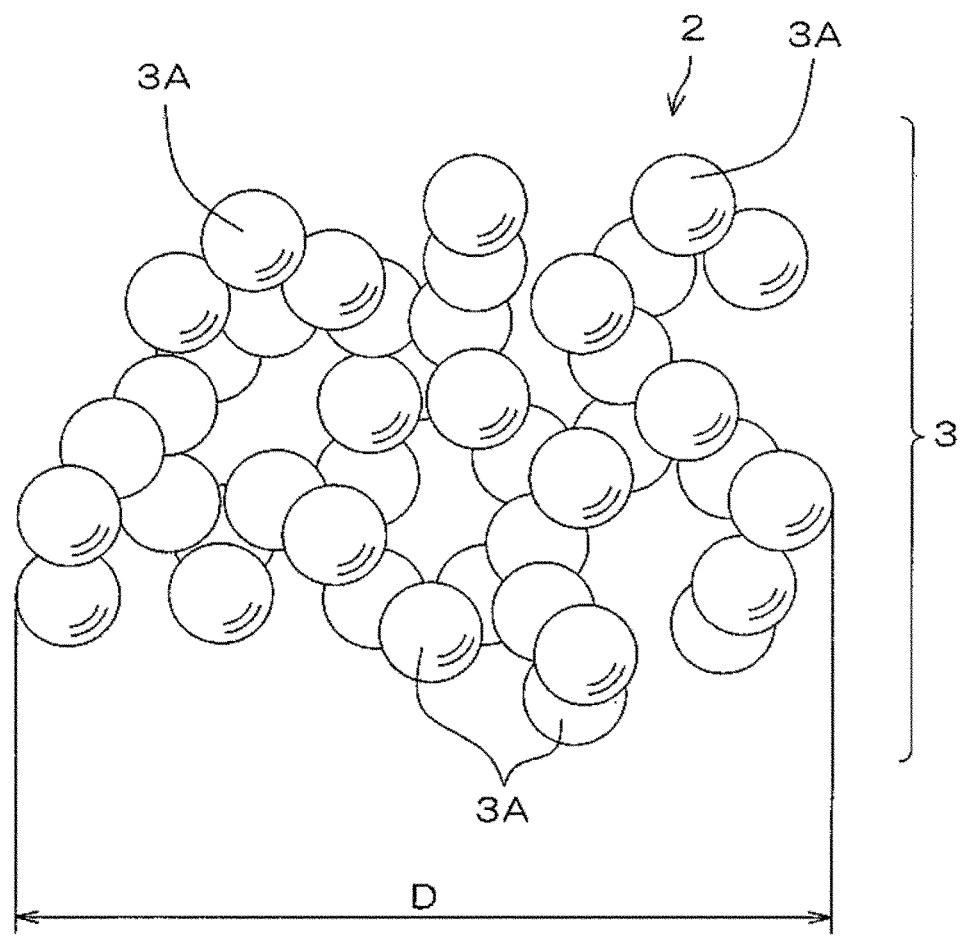
FIG. 1 schematically illustrates one example of a particulate structure of silica constituted by gelation method silica.

FIG. 1 schematically illustrates one example of a particulate structure of silica constituted by gelation method silica. Silica 2, which is constituted by gelation method silica, has a particulate structure such that, for example, a plurality of primary particles (skeleton grains) 3A are grouped in the form of a bunch of grapes to form a secondary particle 3.

In the following descriptions, the specific surface area of silica refers to surface area per unit mass. The surface area of silica is the sum of the external surface area and the internal surface area (i.e., the surface area of the walls of pores in the silica) of silica. The pore volume of silica refers to the volume of pores in silica per unit mass. The mean pore size of silica refers to the mean of the diameters of the pores (cavities) in silica. The mean particle size of silica refers to the mean of diameters D (see FIG. 5) of secondary particles.

The specific surface area of the silica is preferably not less than 20 $m^2/g$ and not more than 1000 $m^2/g$, particularly preferably not less than 100 $m^2/g$ and not more than 700 $m^2/g$. The pore volume of the silica is preferably not less than 0.2 ml/g and not more than 2.0 ml/g, particularly preferably not less than 0.3 ml/g and not more than 1.2 ml/g. The mean pore size of the silica is preferably not less than 2 nm and not greater than 100 nm, particularly preferably not less than 2 nm and not greater than 30 nm. The mean particle size of the silica is preferably not less than 1 μm and not greater than 50 μm, particularly preferably not less than 2 μm and not greater than 30 μm.

Figure 2:
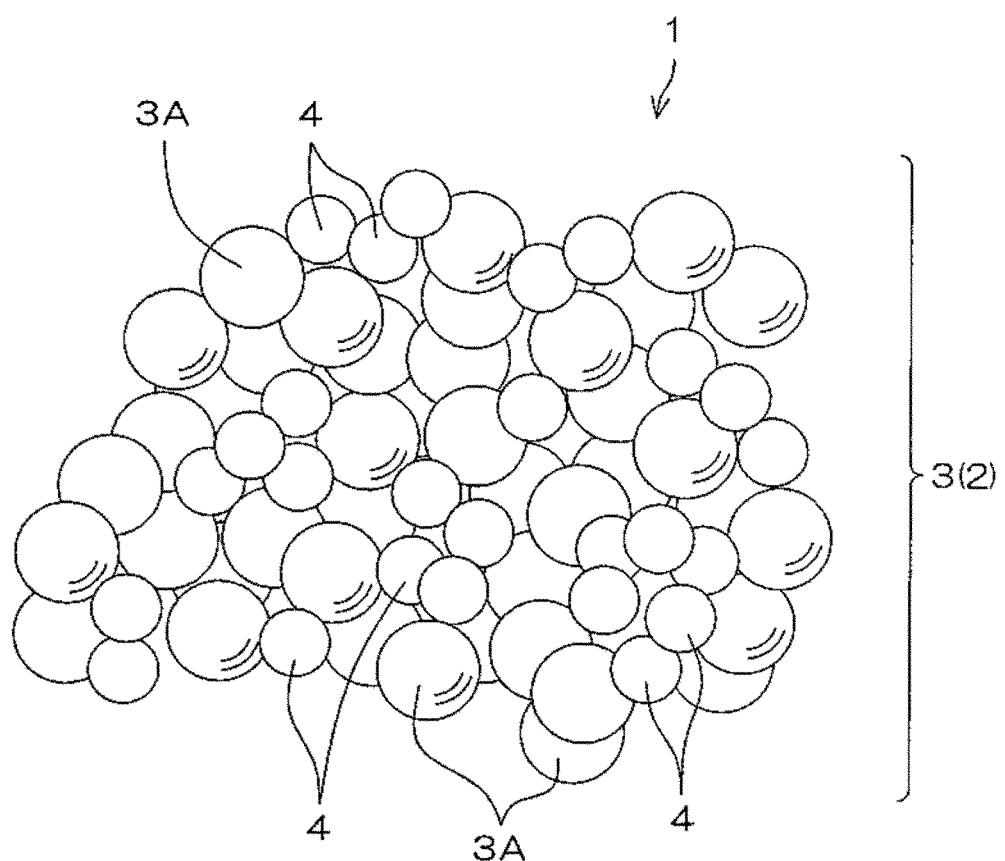
FIG. 2 schematically illustrates one example of a particulate structure of an electrode material which is constituted by: silica constituted by gelation method silica; and silver chloride supported on the silica.

FIG. 2 schematically illustrates one example of a particulate structure of an electrode material which is constituted by: silica constituted by gelation method silica; and silver chloride supported on the silica. The electrode material 1 illustrated in FIG. 2 includes: the silica 2; and silver chloride 4 supported on the surface (including the walls of pores) of the silica 2.

The electrode material in accordance with the present embodiment is produced by, for example, a production method discussed below. The production method includes the steps of: producing a silver compound solution by dissolving a silver compound in a solvent; and allowing the silver compound to be supported on a porous support (including the walls of pores) with the use of the silver compound solution. The silver compound used here is silver nitrate, silver chloride, or the like.

For example, in a case where the silver compound is silver nitrate, a silver nitrate solution is first produced by dissolving silver nitrate powder in an aqueous solvent. Next, the silver nitrate solution is used to allow silver nitrate to be supported on a porous support. A method used to allow silver nitrate to be supported on a porous support is, for example, precipitation, gelatinization, impregnation, ion exchange, or the like method. Then, the silver nitrate supported on the porous support is allowed to react with a chloride-ion-containing compound such as hydrochloric acid or sodium chloride, and thereby silver chloride is supported on the porous support.

For example, in a case where the silver compound is silver chloride, a silver chloride solution is first produced by dissolving silver chloride powder in an aqueous solution such as ammonia water, a concentrated hydrochloric acid solution, an aqueous alkaline cyanide solution, an aqueous thiosulfate solution, or an aqueous ammonium carbonate solution. Next, the silver chloride solution is used to allow silver chloride to be supported on a porous support. A method used to allow silver chloride to be supported on a porous support is, for example, precipitation, gelatinization, impregnation, ion exchange, or the like method. Then, an organic solvent that dissolves in an aqueous solvent, such as methanol, ethanol, isopropyl alcohol, methyl cellosolve, or butyl cellosolve, is added to the silver chloride supported on the porous support, and thereby the silver chloride is supported on the porous support.

Example 1 of Electrode Material

Example 1 includes: silica which is gelation method silica (SYLYSIA710 (trade name) available from FUJI SILYSIA CHEMICAL LTD.); and silver chloride (AgCl) supported on the silica. The silica (silicon dioxide) content of Example 1 is 61 wt %, and the silver chloride content of Example 1 is 39 wt %. In Example 1, the specific surface area of the silica is 397 $m^2/g$, and the mean particle size of the silica is 2.9 μm.

The following description discusses a method of producing Example 1. First, 40 g of silver nitrate powder was dissolved in 50 ml of ion-exchanged water to prepare a silver nitrate solution. Next, 20 g of silica (SYLYSIA710 (trade name) available from FUJI SILYSIA CHEMICAL LTD.) was added to the silver nitrate solution and stirred for 4 hours. Next, a solid component was collected from the stirred solution with the use of type 5A filter paper, and the collected solid component was dried in a shelf-type dryer at 120° C. for 16 hours. In this way, silica-supported silver nitrate, which is constituted by: a silica support; and silver nitrate supported on the silica support, was obtained.

Next, about 34 g of the silica-supported silver nitrate was added to 200 ml of 1M hydrochloric acid, and stirred for 4 hours. Next, a solid component was collected from the stirred solution with the use of type 5A filter paper, and the collected solid component was washed with 200 ml of ion-exchanged water. Next, the washed solid component was dried in a shelf-type dryer at 120° C. for 16 hours, and then was pulverized. In this way, about 30 g of a silica support supporting silver chloride (silica-supported silver chloride) was obtained.

The subject matter in accordance with the present embodiment can be modified in various manners within the matters described in claims.

Features like those described below can further be selected from this specification.

A1. A method of producing an electrode material containing a porous support and silver chloride supported on the porous support, the method including: a first step including producing a silver nitrate solution by dissolving silver nitrate powder in an aqueous solvent; a second step including allowing silver nitrate to be supported on a porous support (including the walls of pores) with use of the silver nitrate solution; and a third step including allowing silver nitrate supported on the porous support to react with a chloride-ion-containing compound and thereby allowing silver chloride to be supported on the porous support.

A2. The method of producing an electrode material according to A1, wherein the chloride-ion-containing compound is hydrochloric acid or sodium chloride.

A3. A method of producing an electrode material containing a porous support and silver chloride supported on the porous support, the method including: a first step including producing a silver chloride solution by dissolving silver chloride; and a second step including allowing silver chloride to be supported on a porous support (including the walls of pores) with use of the silver chloride solution.

A4. The method of producing an electrode material according to A3, further including a third step including adding an organic solvent to the silver chloride supported on the porous support and thereby allowing the silver chloride to be supported on the porous support.

A5. The method of producing an electrode material according to A4, wherein the organic solvent is an organic solvent that dissolves in an aqueous solvent.

A6. The method of producing an electrode material according to A5, wherein the organic solvent is one selected from methanol, ethanol, isopropyl alcohol, methyl cellosolve, butyl cellosolve, and the like.

A7. The method of producing an electrode material according to any of A3 to A6, wherein the aqueous solution is one selected from ammonia water, concentrated hydrochloric acid solutions, aqueous alkaline cyanide solutions, aqueous thiosulfate solutions, and aqueous ammonium carbonate solutions.

A8. The method of producing an electrode material according to any of A1 to A7, wherein the porous support is silica.

A9. The method of producing an electrode material according to A8, wherein the porous support is gelation method silica.

[Recap]

An electrode material in accordance with Aspect 2 of the present invention is arranged such that, in Aspect 1, the porous support is constituted by silica.

Silver chloride agglomerates easily (has low dispersibility), whereas silica does not easily agglomerate (has high dispersibility). According to the above arrangement, it is possible to obtain an electrode material having high dispersibility.

An electrode material in accordance with Aspect 3 of the present invention is arranged such that, in Aspect 1 or 2, an amount of the silver chloride supported on the porous support is not less than 1 wt % and not more than 80 wt %.

The present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST

1 Electrode material
2 Silica
3 Secondary particle
3A Primary particle
4 Silver chloride

The invention claimed is:

1. A bio-electrode material comprising: a porous support; and silver chloride supported on the porous support, wherein the porous support consists of silica, and wherein a mean particle size of the silica is not less than 2 μm and not greater than 30 μm.

2. The bio-electrode material according to claim 1, wherein an amount of the silver chloride supported on the porous support is not less than 1 wt % and not more than 80 wt %.

3. The bio-electrode material according to claim 1, wherein a mean pore size of the silica is not less than 2 nm and not greater than 100 nm.

* * * * *